United States Patent
Randolph et al.

(10) Patent No.: US 6,265,630 B1
(45) Date of Patent: Jul. 24, 2001

(54) PROCESS FOR PENTANE DISPROPORTIONATION

(75) Inventors: Bruce B. Randolph; Marvin M. Johnson, both of Bartlesville, OK (US)

(73) Assignee: Phillips Petroleum Company, Bartlesville, OK (US)

(*) Notice: Subject to any disclaimer, the term of this patent is extended or adjusted under 35 U.S.C. 154(b) by 0 days.

(21) Appl. No.: 09/224,228

(22) Filed: Dec. 30, 1998

(51) Int. Cl.$^7$ ........................................................... C07C 6/08
(52) U.S. Cl. ........................................... 585/708; 585/700
(58) Field of Search ..................................... 585/708, 700

(56) References Cited

U.S. PATENT DOCUMENTS

| | | | |
|---|---|---|---|
| 3,679,771 | * 7/1972 | Hutson, Jr. et al. | 585/708 |
| 4,064,189 | * 12/1977 | Siskin et al. | 585/708 |
| 4,069,268 | 1/1978 | Siskin et al. | 260/666 P |
| 4,120,912 | 10/1978 | Hulme | 260/683.4 |
| 4,472,268 | * 9/1984 | Olah | 208/134 |
| 5,449,843 | 9/1995 | Achord et al. | 570/168 |
| 5,489,727 | * 2/1996 | Randolph et al. | 585/702 |

FOREIGN PATENT DOCUMENTS

2650309 * 5/1977 (DE).

* cited by examiner

*Primary Examiner*—Walter D. Griffin
(74) *Attorney, Agent, or Firm*—Richmond, Hitchcock, Fish & Dollar

(57) ABSTRACT

A process for the disproportionation of pentane to alkanes containing fewer carbon atoms per molecule and alkanes containing more atoms per molecule in the presence of a catalyst composition containing hydrogen fluoride (HF), titanium tetrafluoride ($TiF_4$) and sulfolane.

6 Claims, No Drawings

PROCESS FOR PENTANE DISPROPORTIONATION

BACKGROUND OF THE INVENTION

The invention relates to processes for the disproportionation of pentane to alkanes containing fewer carbon atoms per molecule and alkanes containing more atoms per molecule in the presence of a catalyst composition. In one of its aspects the invention relates to the production of isobutane and isohexanes from a pentane-containing feedstock. In another of its aspects the invention relates to the use of a catalyst combining hydrofluoric acid (HF) with titanium tetrafluoride ($TiF_4$) in the catalytic disproportionation of pentane. In another of its aspects the invention relates to the use of a sulfone diluent in combination with a disproportionation catalyst. In yet another of its aspects the invention also relates to a process for increasing the conversion of a pentane feedstock to desirable isobutanes and isohexanes.

It is known that generally Bronsted acids and Lewis acids can be used with a sulfone diluent as an effective catalyst combination for disproportionation of hydrocarbons, particularly with the use of hydrogen as a co-feed to the process. The present invention, however, provides within certain ranges of operating conditions the specific combination of hydrofluoric acid (a Bronsted acid), titanium tetrafluoride (a Lewis acid) and sulfolane (a sulfone diluent) that provides an unexpectedly effective catalyst for the disproportionation of pentane without the use of hydrogen as a co-feed to the process.

SUMMARY OF THE INVENTION

It is an object of this invention to at least partially convert pentane to alkanes having a fewer number of atoms per molecule, particularly isobutane, and to alkanes having a greater number of atoms per molecule, particularly isohexanes.

Another object of this invention is to employ a catalyst composition in the conversion of pentane by disproportionation to give an improved yield of isobutane and isohexane.

A further object of this invention is to provide the parameters within which the inventive catalyst composition can be most effectively employed to maximize conversion of pentane more specifically to isobutane or to isohexane.

In accordance with this invention a catalyst composition that is a mixture of two catalyst components, (1) hydrofluoric acid (HF) and (2) titanium tetrafluoride ($TiF_4$), and (3) a sulfone diluent, preferably sulfolane, is employed at effective disproportionation conditions to convert pentane to alkanes having a fewer number of atoms per molecule, particularly isobutane, and to alkanes having a greater number of atoms per molecule, particularly isohexanes.

Other objects and advantages of the invention will become apparent from the detailed description and the appended claims.

DETAILED DESCRIPTION OF THE INVENTION

The feed to the process of this invention can be any hydrocarbon-containing mixture that contains at least one pentane, either n-pentane or isopentane, preferably isopentane (2-methylbutane or [neopentane], or mixtures thereof. Generally, the feed contains more than about 50 weight-% pentane, preferably about 60–99.99 weight-% pentane. The feed can contain other hydrocarbons that do not interfere with the process of this invention, i.e. minor amounts of other alkanes, such as n-butane, isobutane, n-hexane and the like, alkenes (monoolefins). Other unsaturated compounds are to be substantially absent from the feed so that side reactions olefin oligomerization, and/or excessive ASO be avoided.

The catalyst composition useful in the process of this invention employs $TiF_4$ in combination with HF with a sulfone diluent present in an amount sufficient to enhance the effectiveness of the catalyst composition in the disproportionation of pentanes. The ratio of the total catalyst composition-$TiF_4$, HF and the sulfone diluent- to the hydrocarbon feed on a weight/weight basis is in the range above about 2:1, preferably above about 3:1, and most preferably from about 2:1 to about 5:1.

Any sulfone that can be effectively combined in solution with HF and $TiF_4$ can be useful in the process of this invention. The sulfones preferred for employment in accordance with this invention include, but are not limited to, 3-methylsulfolane, 2,4-dimethylsulfolane and tetramethylenesulfone (sulfolane). Of these, sulfolane is currently most preferred.

Generally, to be effective, diluents are present in compositions in relatively large amounts. In the process of the present invention, however, the effective quantity of sulfone present in the catalyst composition ranges in an amount up to a ratio of sulfone:acid (HF and $TiF_4$) of about 1:10 (volume/volume) for efficient conversions, particularly in the lower portion of the reaction temperature range.

The catalyst compounds, hydrofluoric acid and titanium tetrafluoride, can be employed in combination in a wide range of weight ratios in catalyst compositions suitable for use in the disproportionation of alkanes. When used, in accordance with this invention, in further combination with a sulfone diluent, the effective weight ratio of HF:sulfone is in a range of at least 9:1, preferably from about 9:1 to about 20:1, more preferably from about 9:1 to about 15:1.

$TiF_4$ is present in the catalytic composition in an amount in the range of about 1.5 mole % to about 10 mole %, preferably from about 3 mole % to about 8 mole %.

The disproportionation reaction temperatures suitable for the process of this invention are generally in the range of about 100° F. (38° C.) to about 190° F. (88° C.), preferably from about 110° F. (43° C.) to about 180° F. (82° C.). The reaction pressure can range from atmospheric to about 1000 psig, preferably from about 100 psig to about 500 psig. The reaction can be carried out as a batch process, as in a stirred autoclave, or as a continuous process. Whether the reaction is performed batchwise or on a continuous basis, the amounts (weight) of the catalyst components and the diluent used is determined by the weight of the hydrocarbon that is to be processed.

The product of the disproportionation reaction contains a variety of substances: HF, $TiF_4$, sulfone diluent, propane, butanes, pentanes, hexanes, heptanes and higher alkanes. These various product components are separated from each other by any suitable means such as fractional distillation, either at an elevated pressure or, after depressurization, at atmospheric conditions. Generally the product is separated to obtain the specific product stream desired and to make the catalyst composition components and unconverted pentane available for recycle.

The following examples are presented to further illustrate this invention and are not to be construed as unduly limiting its scope.

EXAMPLE I

For run 1, a Monel autoclave reactor (volume: 300 ml) equipped with a mechanical stirrer, a thermocouple, a pressure gauge and various valves, was charged with about 90 gm of anhydrous hydrogen fluoride (HF), and about 6.2 gm of $TiF_4$. The mixture was stirred at a rate of 500 rpm as the temperature was raised to about 123° F. (51° C.). Thereafter 65.6 gm of a hydrocarbon feed containing 99.2 percent by weight isopentane was added to the reactor.

After a reaction time of 30 minutes, at a reaction pressure of 250 psig (about 17.2 atm. gauge) at the reaction temperature of about 123° F. (51° C.), the stirring was stopped and the product was withdrawn from the reactor. The product was allowed to settle and then was passed through a column of alumina beads to remove soluble HF. The product was analyzed by means of gas chromatography.

In Tables I–IV that follow, due to the confining space, the following abbreviations (aside from the obvious "Temp" for temperature and "Conv" for conversion) were used: "Dil" indicates sulfolane used as the diluent in the catalyst composition, "Comp" indicates the total of the catalyst composition (HF, $TiF_4$ and sulfolane), "Prod" indicates product, "Sel" indicates selectivity, "w/w" indicates weight/weight and "v/v" indicates volume/volume. Selectivity is defined as weight of $iC_4$ or $C_6$ per weight of $C_5$ converted.

In Table I all of the runs were conducted at a pressure of 250 psig, had a sulfolane:catalyst ratio of less than 0.1 and, with the exception of runs 1 and 2 which used a $TiF_4$:HF molar ratio of 0.01, used a $TiF_4$:HF molar ratio of 0.05. Similarly, all the runs had a contact time of 30 minutes and with the exception of control runs 10–12, which used a stir rate of 1500 rpm, used a stir rate of 500 rpm. All of the other data pertinent to the example runs are collected in the table.

TABLE I

Pentane Disproportionation with $TiF_4$/HF Catalyst and Sulfolane Diluent

| Run | Temp °F. | $TiF_4$ gm | Dil gm | HF gm | HF/Dil (w/w) | Dil/Acid (v/v) | Mole % $TiF_4$ | Comp/Feed (w/w) | $iC_5$ Feed Wt % | $nC_5$ Feed Wt % | $iC_4$ Prod Wt % | $C_5$ Prod Wt % | $C_6$ Prod Wt % | $iC_5$ Conv % | $iC_4$ Sel | $C_6$ Sel |
|---|---|---|---|---|---|---|---|---|---|---|---|---|---|---|---|---|
| 1 | 123.5 | 6.2 | 0 | 89.9 | 0 | 0 | 1.10 | 1.5 | 99.2 | 0.67 | 2.1 | 96.2 | 1.3 | 3.8 | 56.6 | 34.4 |
| 2 | 124.3 | 6.2 | 10.1 | 89.7 | 8.9 | 0.09 | 1.08 | 1.6 | 99.2 | 0.67 | 0.5 | 97.9 | 0.9 | 2.0 | 25.7 | 43.7 |
| 3 | 119.6 | 29.8 | 9.9 | 90.3 | 9.1 | 0.08 | 4.97 | 1.9 | 99.2 | 0.67 | 19.7 | 59.3 | 14.3 | 43.9 | 45.2 | 32.8 |
| 4 | 127.8 | 29.8 | 9.9 | 90.3 | 9.1 | 0.08 | 4.97 | 2.0 | 0.4 | 99.3 | 19.7 | 63.4 | 7.5 | 50.4 | 39.4 | 14.4 |
| 5 | 127.6 | 29.8 | 9.9 | 90.3 | 9.1 | 0.08 | 4.97 | 2.0 | 99.2 | 0.67 | 23.8 | 53.5 | 11.6 | 50.7 | 47.4 | 23.0 |
| 6 | 128.0 | 29.8 | 9.9 | 90.3 | 9.1 | 0.08 | 4.97 | 2.0 | 99.2 | 0.67 | 12.0 | 71.2 | 9.6 | 29.8 | 40.6 | 32.2 |
| 7 | 117.9 | 29.8 | 9.9 | 90.3 | 9.1 | 0.08 | 4.97 | 2.0 | 99.2 | 0.67 | 14.0 | 66.0 | 11.4 | 35.1 | 40.0 | 32.7 |
| 8 | 120.1 | 29.8 | 9.9 | 90.3 | 9.1 | 0.08 | 4.97 | 2.0 | 99.2 | 0.68 | 10.9 | 68.6 | 10.5 | 32.6 | 33.8 | 32.4 |
| 9 | 118.1 | 29.8 | 9.9 | 98.3 | 9.1 | 0.08 | 4.97 | 2.0 | 99.2 | 0.68 | 8.3 | 76.0 | 9.5 | 24.8 | 33.4 | 38.5 |
| 10 | 102.4 | 0 | 0 | 159.3 | — | — | — | 3.2 | 99.0 | 0.32 | 0.2 | 99.8 | 1.0 | 0.9 | 17.9 | 32.1 |
| 11 | 182.0 | 0 | 0 | 127.2 | — | — | — | 2.9 | 98.6 | 0.62 | 2.3 | 93.0 | 4.1 | 6.6 | 34.8 | 52.9 |
| 12 | 195.0 | 0 | 0 | 108.2 | — | — | — | 2.0 | 99.0 | 0.38 | 7.1 | 80.3 | 11.1 | 19.8 | 35.6 | 56.3 |

In Table I the data for runs 1 and 2 show that in catalyst composition mixtures containing about 1 mole % $TiF_4$ the addition of sulfolane has the effect at temperatures near 123° F. of causing conversion to drop from 3.8% to 2.0%. In runs 3 and 4 the addition of about 5 mole % $TiF_4$ to the mixture increases conversion to greater than 40 percent and produces a catalyst that stays active through five additional batch runs to have a final conversion of about 25 percent in run 9. Note that in run 4 the feedstock is n-pentane.

Table I also shows in comparative runs 10–12 the effect of a catalyst system using HF alone as the reaction temperature is raised from about 100° F. to about 200° F. Note that the pentane conversion rises only to about 20 percent at a reaction temperature of about 200° F. while using a catalyst composition having the components of this invention reaches a pentane conversion of about 50 percent at much lower reaction temperatures.

EXAMPLE II

In Table II all of the runs were conducted at a pressure of 250 psig, had a sulfolane:catalyst ratio of 0.3 and, with the exception of runs 13 and 14 which used a $TiF_4$:HF molar ratio of 0.01, used a $TiF_4$:HF molar ratio of 0.05. Similarly, all the runs had a contact time of 30 minutes and with the exception of run 16, which used a stir rate of 1500 rpm, used a stir rate of 500 rpm. All of the other data pertinent to the example runs are collected in the table.

TABLE II

Pentane Disproportionation with TiF$_4$/HF Catalyst and Sulfolane Diluent

| Run | Temp °F. | TiF$_4$ gm | Dil gm | HF gm | HF/Dil (w/w) | Dil/Acid (v/v) | Mole % TiF$_4$ | Comp/Feed (w/w) | iC$_5$ Feed Wt % | nC$_5$ Feed Wt % | iC$_4$ Feed Wt % | C$_5$ Prod Wt % | C$_6$ Prod Wt % | iC$_5$ Prod Wt % | iC$_4$ Conv % | C$_6$ Sel % | Sel % |
|---|---|---|---|---|---|---|---|---|---|---|---|---|---|---|---|---|---|
| 13 | 122.5 | 4.6 | 29.7 | 70.9 | 2.4 | 0.3 | 1.0 | 1.6 | 99.2 | 0.7 | 0.1 | 99.3 | 0.3 | 0.5 | 22.2 | 40.2 |
| 14 | 115.6 | 4.6 | 29.7 | 70.9 | 2.4 | 0.3 | 1.0 | 1.6 | 99.2 | 0.7 | 0.2 | 99.2 | 0.3 | 0.6 | 22.2 | 38.1 |
| 15 | 125.0 | 19.7 | 24.1 | 62.6 | 2.6 | 0.3 | 4.6 | 2.0 | 99.0 | 0.7 | 0.1 | 98.3 | 0.1 | 0.7 | 12.4 | 3.8 |
| 16 | 124.0 | 19.7 | 24.1 | 62.6 | 2.6 | 0.3 | 4.6 | 2.0 | 99.1 | 0.7 | 0.1 | 98.2 | 0.1 | 1.5 | 2.9 | 3.2 |
| 17 | 182.6 | 19.7 | 24.2 | 62.5 | 2.6 | 0.3 | 4.6 | 2.0 | 98.0 | 0.7 | 7.2 | 82.5 | 8.0 | 18.3 | 40.0 | 44.4 |
| 18 | 171.0 | 19.7 | 24.2 | 62.5 | 2.6 | 0.3 | 4.6 | 2.0 | 98.0 | 0.7 | 6.6 | 85.3 | 5.7 | 14.5 | 46.4 | 39.8 |

Table II shows the results for catalyst compositions with a sulfolane:catalyst ratio of 0.3 (volume/volume) and with HF:sulfolane ratios lowered to about 2.6 (weight/weight). In runs 13 and 14, with about 1 mole % TiF$_4$, essentially no conversion occurred. Increasing the TiF$_4$ concentration to 4.6 mole % (runs 15–18) had little effect on the conversion. A temperature increase to 170° F. or more (runs 17 and 18) was required to produce significant conversion.

EXAMPLE III

In Table III all of the runs were conducted at a pressure of 250 psig, had a sulfolane:catalyst ratio of 0.8 and used a TiF$_4$:HF molar ratio of 0.05. Similarly, all the runs had a contact time of 30 minutes with the exception of runs 19–21 which used a 15 minute contact time. All the runs used a stir rate of 1500 rpm. All of the other data pertinent to the example runs are collected in the table.

the catalyst composition:hydrocarbon feed ratio was minimal. The contact time was doubled to 30 minutes for runs 22–25 with a three-fold increase in conversion shown in run 22. For runs 23–25 the reaction temperature was raised to about 160° F. with conversion increases even though there was a steady decrease in conversion through these runs due to catalyst deactivation. Note that an increase in contact time increased the iC$_4$ selectivity and decreased the C$_6$ selectivity.

For runs 26–28 the HF:sulfolane ratio was raised above 9.1. A 2:1 catalyst composition:hydrocarbon feed ratio yielded only a 16.4 percent conversion (run 26) while raising the catalyst composition:hydrocarbon feed ratio to 3 (run 27) gave a three-fold increase in conversion to 46.7 percent which then was decreased to about 21 percent (run 28) with a catalyst composition:hydrocarbon feed ratio of 1.5. These values indicate that better results are obtained using lower sulfolane:acid ratios.

TABLE III

Pentane Disproportionation with TiF$_4$/HF Catalyst and Sulfolane Diluent

| Run | Temp °F. | TiF$_4$ gm | Dil gm | HF gm | HF/Dil (w/w) | Dil/Acid (v/v) | Mole % TiF$_4$ | Comp/Feed (w/w) | iC$_5$ Feed Wt % | nC$_5$ Feed Wt % | iC$_4$ Prod Wt % | C$_5$ Prod Wt % | C$_6$ Prod Wt % | iC$_5$ Conv % | iC$_4$ Sel % | C$_6$ Sel % |
|---|---|---|---|---|---|---|---|---|---|---|---|---|---|---|---|---|
| 19 | 120.0 | 14.9 | 5.1 | 45.6 | 9.0 | 0.08 | 3.7 | 2.0 | 99.1 | 0.7 | 2.7 | 92.1 | 4.9 | 9.0 | 30.1 | 54.7 |
| 20 | 118.8 | 14.9 | 5.1 | 45.6 | 9.0 | 0.08 | 3.7 | 1.0 | 99.1 | 0.7 | 3.0 | 92.7 | 3.6 | 7.7 | 39.4 | 45.9 |
| 21 | 115.9 | 14.9 | 5.1 | 45.6 | 9.0 | 0.08 | 3.7 | 0.7 | 99.1 | 0.7 | 2.9 | 92.9 | 3.5 | 7.3 | 39.7 | 47.9 |
| 22 | 120.1 | 14.9 | 5.1 | 45.6 | 9.0 | 0.08 | 3.7 | 2.0 | 99.1 | 0.7 | 9.5 | 78.7 | 8.2 | 22.4 | 42.8 | 36.6 |
| 23 | 160.2 | 14.9 | 5.1 | 45.6 | 9.0 | 0.08 | 3.7 | 2.0 | 99.1 | 0.7 | 16.7 | 61.8 | 15.7 | 41.3 | 40.7 | 38.3 |
| 24 | 161.7 | 14.9 | 5.1 | 45.6 | 9.0 | 0.08 | 3.7 | 2.0 | 99.1 | 0.7 | 13.8 | 69.3 | 11.6 | 33.2 | 41.9 | 35.3 |
| 25 | 159.7 | 14.9 | 5.1 | 45.6 | 9.0 | 0.08 | 3.7 | 2.0 | 99.1 | 0.7 | 12.1 | 73.3 | 9.8 | 28.5 | 43.0 | 34.5 |
| 26 | 118.8 | 29.8 | 9.8 | 90.0 | 9.2 | 0.08 | 3.7 | 2.0 | 99.1 | 0.7 | 5.2 | 86.0 | 8.1 | 16.4 | 32.0 | 49.4 |
| 27 | 119.8 | 29.8 | 9.8 | 90.0 | 9.2 | 0.08 | 3.7 | 3.0 | 99.1 | 0.7 | 17.7 | 57.8 | 19.4 | 46.7 | 38.2 | 41.8 |
| 28 | 115.9 | 29.8 | 9.8 | 90.0 | 9.2 | 0.08 | 3.7 | 1.5 | 99.1 | 0.7 | 8.1 | 81.3 | 8.5 | 20.6 | 39.3 | 41.1 |

In Table III the HF:sulfolane ratio was about 9.0 (weight/weight), the sulfolane:acid ratio was 0.08 (volume/volume) and the TiF$_4$ concentration was 3.7 mole % which is intermediate between the 1 and 5 mole % shown in Tables I and II. In runs 19–21, which used a 15 minute contact time and reaction temperature of up to about 120° F., the effect of

EXAMPLE IV

A series of test runs was conducted using ZrF$_4$ to replace TiF$_4$ as part of the catalyst composition. The runs were carried out at reaction conditions commensurate with the tests above. The pertinent data is reported in Table IV.

TABLE IV

Pentane Disproportionation with Catalyst Containing $ZrF_4$

| Run | Temp °F | $ZrF_4$ gm | Dil gm | HF gm | HF/Dil (w/w) | Mole % $ZrF_4$ | Comp/Feed (w/w) | $iC_5$ Feed Wt % | $nC_5$ Feed Wt % | $iC_4$ Prod Wt % | $C_5$ Prod Wt % | $C_6$ Prod Wt % | $iC_5$ Conv % |
|---|---|---|---|---|---|---|---|---|---|---|---|---|---|
| 29 | 130.8 | 26.6 | 24.1 | 62.5 | 2.6 | 4.6 | 2.0 | 99.0 | 0.7 | 0.2 | 98.3 | 1.1 | 1.9 |
| 30 | 162.6 | 26.6 | 24.1 | 62.5 | 2.6 | 4.6 | 2.0 | 99.0 | 0.7 | 0.3 | 98.5 | 0.9 | 1.5 |
| 31 | 120.6 | 30.2 | 16.6 | 65.4 | 3.9 | 5.0 | 2.0 | 99.0 | 0.7 | 0.1 | 99.6 | 0.1 | 0.1 |
| 32 | 160.8 | 30.2 | 16.6 | 65.4 | 3.9 | 5.0 | 2.0 | 99.0 | 0.7 | 0.6 | 98.0 | 1.1 | 1.8 |
| 33 | 124.4 | 30.2 | 0 | 70.6 | — | 4.9 | 2.0 | 99.0 | 0.7 | 0.2 | 99.2 | 0.4 | 0.5 |
| 34 | 164.4 | 30.2 | 0 | 70.6 | — | 4.9 | 2.0 | 99.0 | 0.7 | 1.1 | 96.7 | 1.7 | 3.1 |

After the tests above, which show there is no catalyst activity, were completed it was found that $ZrF_4$ is essentially insoluble in both HF and sulfolane. An inspection of the reactor contents showed that the $ZrF_4$ had settled out into the bottom of the reactor.

Reasonable variations, modifications and adaptations can be made within the scope of the disclosure and the appended claims without departing from the scope of this invention.

What is claimed is:

1. A process for disproportionating pentanes in a hydrocarbon feedstock to form alkanes containing fewer than five carbon atoms and alkanes containing more than five carbon atoms wherein the process comprises:

(1) contacting pentanes in a hydrocarbon feedstock with a catalyst composition comprising:
       (A) hydrofluoric acid (HF),
       (B) titanium tetrafluoride ($TiF_4$) and
       (C) a sulfone diluent
    wherein the catalyst composition is present in a catalyst composition:hydrocarbon feedstock weight ratio greater than about 2:1,
    $TiF_4$ is present in the catalytic composition in an amount in the range of about 1.5 mole % to about 10 mole %, sulfone in the catalyst composition ranges in an amount up to a ratio of sulfone:acid (HF and $TiF_4$) of about 1:10 (volume/volume), the weight ratio of HF:sulfone is at least 9:1, the reaction temperature for the process is in the range of about 100° F. (38° C.) to about 190° F. (88° C.) and the reaction pressure for the process is in the range from atmospheric to about 1000 psig and (2) recovering alkanes containing more than five carbon atoms and alkanes containing more than five carbon atoms.

2. A process according to claim 1 wherein the catalyst composition:hydrocarbon feedstock weight ratio is greater than about 3:1.

3. A process according to claim 1 wherein the catalyst composition:hydrocarbon feedstock weight ratio is in a range from about 2:1 to about 5:1.

4. A process according to claim 1 wherein the sulfone is tetramethylenesulfone(sulfolane).

5. A process according to claim 2 wherein the sulfone is tetramethylenesulfone(sulfolane).

6. A process according to claim 3 wherein the sulfone is tetramethylenesulfone(sulfolane).

* * * * *

UNITED STATES PATENT AND TRADEMARK OFFICE
CERTIFICATE OF CORRECTION

PATENT NO.   : 6,265,630 B1
DATED        : July 24, 2001
INVENTOR(S)  : Bruce B. Randolph and Marvin M. Johnson It is certified that error appears in the above-identified patent and that said Letters Patent is hereby corrected as shown below:

Column 8,
Line 22, please delete "more" and insert therefor -- fewer --.

Signed and Sealed this

Sixth Day of August, 2002

Attest:

JAMES E. ROGAN
Attesting Officer    Director of the United States Patent and Trademark Office